United States Patent
Kim et al.

(10) Patent No.: US 7,524,896 B2
(45) Date of Patent: Apr. 28, 2009

(54) HYDROXYPIVALYL HYDROXYPIVALATE ESTER PLASTICIZER COMPOSITION AND METHOD OF PREPARING THE SAME

(75) Inventors: Hyunkyu Kim, Daejeon (KR); Kyeseok Lee, Daejeon (KR); Kyu Il Lee, Daejeon (KR); Byoungkue Chun, Daejeon (KR)

(73) Assignee: LG Chem, Ltd. (KR)

( * ) Notice: Subject to any disclaimer, the term of this patent is extended or adjusted under 35 U.S.C. 154(b) by 321 days.

(21) Appl. No.: 11/487,855

(22) Filed: Jul. 17, 2006

(65) Prior Publication Data

US 2007/0015933 A1    Jan. 18, 2007

(30) Foreign Application Priority Data

Jul. 15, 2005  (KR) .................. 10-2005-0064151
Mar. 2, 2006   (KR) .................. 10-2006-0019911

(51) Int. Cl.
*C08K 5/101*  (2006.01)
*C08L 27/06*  (2006.01)

(52) U.S. Cl. .......... 524/569; 524/293; 524/299; 524/306; 524/321; 524/567; 585/438; 585/600

(58) Field of Classification Search .......... 524/293, 524/299, 306, 321, 567, 569; 585/438, 600
See application file for complete search history.

(56) References Cited

U.S. PATENT DOCUMENTS 4,666,965 A *  5/1987  Aoki .................. 524/114
5,281,647 A    1/1994  Eapen
6,001,910 A   12/1999  Blumenthal et al.
6,703,436 B2 *  3/2004  Lee et al. .................. 524/306
2003/0096942 A1  5/2003  Jen

FOREIGN PATENT DOCUMENTS

| EP | 0 420 770 | 11/1994 |
| JP | 58-140044 | 8/1983 |
| JP | 59-232114 | 12/1984 |
| RO | 62655 | 8/1973 |

OTHER PUBLICATIONS

Complex Esters of 2, 2-Dimethylhydracrylic Acid, Henry F. Lederle, Olin Mathieson Chem I & EC Product Research and Development, vol. 8 No. ! Mar. 1969.*
PCT International Search Report—PCT International Application No. PCT/KR2006/002733—Date of Mailing: Oct. 17, 2006.
European Search Report—PCT Application No. PCT/KR2006002733—Dated Apr. 9, 2008.

* cited by examiner

*Primary Examiner*—Peter Szekely
(74) *Attorney, Agent, or Firm*—Cantor Colburn LLP

(57) ABSTRACT

Provided are a plasticizer composition including a hydroxypivalyl hydroxypivalate ester and a neopentylglycol ester, and a method of preparing the plasticizer composition. The plasticizer composition provides a polyvinyl chloride resin having excellent properties of heat loss, migration resistance and plasticization efficiency, and tensile strength, elongation, etc.

16 Claims, No Drawings

HYDROXYPIVALYL HYDROXYPIVALATE ESTER PLASTICIZER COMPOSITION AND METHOD OF PREPARING THE SAME

CROSS-REFERENCE TO RELATED PATENT APPLICATION

This application claims the benefit of Korean Patent Application Nos. 10-2005-0064151, filed on Jul. 15, 2005, and 10-2006-0019911, filed on Mar. 2, 2006 in the Korean Intellectual Property Office, the disclosure of which is incorporated herein in its entirety by reference.

BACKGROUND OF THE INVENTION

1. Field of the Invention

The present invention relates to a hydroxypivalyl hydroxypivalate ester plasticizer composition, and more particularly, to a hydroxypivalyl hydroxypivalate ester plasticizer composition that is used as a plasticizer for a polyvinyl chloride (PVC) resin.

2. Description of the Related Art

Polyvinyl chloride resins are polymers of vinyl chloride monomers or copolymers containing 50% or more of vinyl chloride, and are widely used resins which are manufactured by extrusion molding, injection molding, calendaring, etc. Polyvinyl chloride resins are used in a wide range of applications, such as pipes, electric wires, electrical and mechanical products, toys, films, sheets, artificial leathers, tarpaulin, tapes, food packaging, and medical products, all of which can be manufactured using the methods described above. Polyvinyl chloride resins may have various properties depending on additives such as plasticizers, stabilizer, fillers, pigments, etc, added in a proper ratio thereto.

Plasticizers added to polyvinyl chloride resins are used to provide workability, flexibility, electric insulation, adhesiveness, etc. to the polyvinyl chloride resins. Examples of such plasticizers include phthalates, adipates, and trimellitates. In particular, phthalates, such as di-ethylhexyl phthalate (DEHP), di-butyl phthalate (DBP), di-isodecyl phthalate (DIDP), butyl benzyl phthalate (BBP), and di-isononyl phthalate (DINP), and adipates such as di-2-ethylhexyl adipate (DEHA) are commonly used.

However, the US Environmental Protection Agency and the National Institute of Health Science in Japan have classified phthalates and adipates as endocrine disruptors. Accordingly, the development of a plasticizer not containing phthalates and adipates is required.

2-ethylhexanoic acid [2-{2-(2-ethylhexanoyloxy)-ethoxy}ethoxy]-ethyl ester obtained by reacting triethylene glycol with 2-ethylhexanoic acid is a plasticizer that does not contain phthalates or adipates. This compound has excellent workability in polymer resin manufacturing processes, but the obtained polymer resin has poor properties in elongation, adhesion, transparency, and the like.

An ester compound obtained by reacting neopentylglycol with butyric acid, 2-ethylhexanoic acid, etc. as an aliphatic acid has been reported for a plasticizer in Rumanian Patent No. 62655. However, the compatibility of the ester compound with respect to polyvinyl chloride resin is lower than that of phthalates, and polyvinyl chloride resin to which the ester compound has been added has low transparency, poor elongation, and poor migration resistance.

SUMMARY OF THE INVENTION

The present invention provides a plasticizer composition not containing known endocrine disruptors phthalates and adipates, and having excellent properties in compatibility with a polymer resin, and providing polymer resin having excellent tensile strength, elongation, hardness, and migration resistance, and a method of preparing the plasticizer composition.

According to an aspect of the present invention, there is provided a hydroxypivalyl hydroxypivalate ester plasticizer composition including: a neopentylglycol ester compound having at least one of the compounds represented by formulae 1 through 3; a hydroxypivalyl hydroxypivalate ester compound having at least one of the compounds represented by formulae 4 through 7; and a hydroxypivalyl hydroxypivalate ester compound having at least one of the compounds represented by formulae 8 through 10.

$$R_1OCO-CH_2C(CH_3)_2CH_2-OCOR_1 \tag{1}$$

$$R_2OCO-CH_2C(CH_3)_2CH_3-OCOR_3 \tag{2}$$

$$R_4OCO-CH_2C(CH_3)_2CH_2\,OCOR_4 \tag{3}$$

$$R_1OCO-CH_2C(CH_3)_2-COO-CH_2C(CH_3)_2-CH_2-OCOR_1 \tag{4}$$

$$R_3OCO-CH_2C(CH_3)_2-COO-CH_2C(CH_3)_2-CH_2-OCOR_2 \tag{5}$$

$$R_2OCO-CH_2C(CH_3)_2-COO-CH_2C(CH_3)_2-CH_2-OCOR_3 \tag{6}$$

$$R_4OCO-CH_2C(CH_3)_2-COO-CH_2C(CH_3)_2-CH_2-OCOR_4 \tag{7}$$

$$R_1OCO-CH_2C(CH_3)_2-COO-CH_2C(CH_3)_2-COO-CH_2C(CH_3)_2-CH_2-OCOR_1 \tag{8}$$

$$R_2OCO-CH_2C(CH_3)_2-COO-CH_2C(CH_3)_2-COO-CH_2C(CH_3)_2-CH_2-OCOR_3 \tag{9}$$

$$R_4OCO-CH_2C(CH_3)_2-COO-CH_2C(CH_3)_2-COO-CH_2C(CH_3)_2-CH_2-OCOR_4 \tag{10}$$

Here, $R_1$ and $R_2$ are each independently a C3-C12 alkyl group, and $R_3$ and $R_4$ are a C6-C10 aryl group.

The hydroxypivalyl hydroxypivalate ester plasticizer composition may include 1 to 50% by weight of the neopentylglycol ester compound having at least one of the compounds represented by formulae 1 through 3; 40 to 90% by weight of the hydroxypivalyl hydroxypivalate ester compound having at least one of the compounds represented by formulae 4 through 7; and 1 to 40% by weight of the a hydroxypivalyl hydroxypivalate ester compound having at least one of the compounds represented by formulae 8 through 10.

The hydroxypivalyl hydroxypivalate ester plasticizer composition may include 2-Ethyl-hexanoic acid 3-(2-ethyl-hexanolyoxy)-2,2-dimethyl-propyl ester, Benzoic acid 3-(2-ethyl-hexanoyloxy)-2,2-dimethyl-propyl ester), Benzoic acid 3-benzoyloxy-2,2-dimethyl-propyl ester), 2-Ethyl-hexanoic acid 2-[3-(2-ethyl-hexanoyloxy)-2,2-dimethyl-propoxycarbonyl]-2-methyl-propyl ester, Benzoic acid 2-[3-(2-ethyl-hexanoyloxy)-2,2-dimethyl-propoxycarbonyl]-2-methyl-propyl ester, Benzoic acid 3-[3-(2-ethyl-hexanoyloxy)-2,2-dimethyl-propionyloxy]-2,2-dimethyl-propyl ester, Benzoic acid 3-[3-(benzoyloxy)-2,2-dimethyl-propionyloxy]-2,2-dimethyl-propyl ester, 2-Ethyl-hexanoic acid 2-{2-[3-(2-ethyl-hexanoyloxy)-2,2-dimethyl-propoxycarbonyl]-2-methyl-propoxycarbonyl}-2-methyl-propyl ester, Benzoic acid 3-{3-[3-(2-ethyl-hexanoyloxy)-2,2-dimethyl-propionyloxy]-2,2-dimethyl-propionyloxy}-2,2dimethyl-propyl ester, and Benzoic acid 3-{3-[3-(benzoyloxy)-2,2-dimethyl-propionyloxy]-2,2-dimethyl-propionyloxy}-2,2-dimethyl-propyl ester.

According to another aspect of the present invention, there is provided a method of preparing a hydroxypivalyl hydroxypivalate ester plasticizer composition, comprising reacting 20 to 50% by weight of a hydroxypivalyl hydroxypivalate; or a mixture of a hydroxypivalyl hydroxypivalate and a neopentylglycol with 50 to 80% by weight of a C3-C12 aliphatic acid; a C6-C10 aromatic acid; or a C3-C12 aliphatic acid and a C6-C10 aromatic acid.

The aliphatic acid may be 2-ethylhexanoic acid, and the aromatic acid may be a benzoic acid.

The hydroxypivalyl hydroxypivalate ester composition may be obtained by reacting at 100 to 300° C. for 4 to 14 hours. 1 to 20 parts by weight of xylene and 0.0001 to 1 parts by weight of tetraisopropyltitanate based on 100 parts by weight of the reactant may further be added to the reaction.

According to another aspect of the present invention, there is provided a polyvinyl chloride resin including the hydroxypivalyl hydroxypivalate ester plasticizer composition.

According to another aspect of the present invention, there is provided a hydroxypivalyl hydroxypivalate ester compound represented by formulae 5, 6, 8, 9 and 10.

The hydroxypivalyl hydroxypivalate ester plasticizer composition of the present invention can be used as a plasticizer during polyvinyl chloride manufacturing process to provide a polyvinyl chloride having excellent properties in tensile strength, elongation, hardness, and migration resistance.

DETAILED DESCRIPTION OF THE INVENTION

The present invention will now be described in detail.

A hydroxypivalyl hydroxypivalate ester plasticizer composition according to an embodiment of the present invention does not include phthalates and adipates that are known as endocrine disruptors and is suitable to be applied to a polyvinyl chloride providing excellent properties in tensile strength, elongation, hardness, and migration resistance. The hydroxypivalyl hydroxypivalate ester plasticizer composition includes: a neopentylglycol ester compound having at least one of the compounds represented by formulae 1 through 3; a hydroxypivalyl hydroxypivalate ester compound having at least one of the compounds represented by formulae 4 through 7; and a hydroxypivalyl hydroxypivalate ester compound having at least one of the compounds represented by formulae 8 through 10.

$$R_1OCO—CH_2C(CH_3)_2CH_2OCOR_1 \quad (1)$$

$$R_2OCO—CH_2C(CH_3)_2CH_2—OCOR_3 \quad (2)$$

$$R_4OCO—CH_2C(CH_3)_2CH_213\ OCOR_{4tm} \quad (3)$$

$$R_1OCO—CH_2C(CH_3)_2—COO—CH_2C(CH_3)_2—CH_2—OCOR_1 \quad (4)$$

$$R_3OCO—CH_2C(CH_3)_2—COO—CH_2C(CH_3)_2—CH_2—OCOR_2 \quad (5)$$

$$R_2OCO—CH_2C(CH_3)_2—COO—CH_2C(CH_3)_2—CH_2—OCOR_3 \quad (6)$$

$$R_4OCO—CH_2C(CH_3)_2—COO—CH_2C(CH_3)_2—CH_2—OCOR_4 \quad (7)$$

$$R_1OCO—CH_2C(CH_3)_2—COO—CH_2C(CH_3)_2—COO—CH_2C(CH_3)_2—CH_2—OCOR_1 \quad (8)$$

$$R_2OCO—CH_2C(CH_3)—COO—CH_2C(CH_3)_2—COO—CH_2C(CH_3)_2—CH_2—OCOR_3 \quad (9)$$

$$R_4OCO—CH_2C(CH_3)_2—COO—CH_2C(CH_3)_2—COO—CH_2C(CH_3)_2—OCOR_4 \quad (10)$$

Here, $R_1$ and $R_2$ are each independently a C3-C12 alkyl group, and $R_3$ and $R_4$ are each independently a C6-C10 aryl group.

The amount of the neopentylglycol ester compound having at least one of the compounds represented by formulae 1 through 3 may be in the range of 1 to 50% by weight of the hydroxypivalyl hydroxypivalate ester plasticizer composition, and more preferably 10 to 40% by weight. When the amount of neopentylglycol ester compound is less than 1% by weight, the plasticization efficiency and other properties of a polyvinyl chloride product to which the plasticizer composition is added can be hindered due to low tensile strength and high hardness. On the other hand, when the amount of neopentylglycol ester compound is greater than 60% by weight, a cling film including the plasticizer composition can have too high adhesivity.

The amount of the hydroxypivalyl hydroxypivalate ester compound having at least one of the compounds represented by formulae 4 through 7 may be in the range of 40 to 90% by weight of the hydroxypivalyl hydroxypivalate ester plasticizer composition, and more preferably 50 to 80% by weight. When the amount of the hydroxypivalyl hydroxypivalate ester compound is less than 40% by weight, the compatibility with polyvinyl chloride resin may decrease. When the amount of hydroxypivalyl hydroxypivalate ester compound is greater than 90% by weight, the obtained resin may have poor properties of tensile strength, elongation, etc.

The amount of the a hydroxypivalyl hydroxypivalate ester compound having at least one of the compounds represented by formulae 8 through 10 may be in the range of 1 to 40% by weight of the hydroxypivalyl hydroxypivalate ester plasticizer composition, and more preferably 5 to 20% by weight. When the hydroxypivalyl hydroxypivalate ester compound is less than 1%, a cling film including the plasticizer composition may get tangled during the cling film manufacturing processes due to having too high adhesivity. On the other hand, when the amount of the hydroxypivalyl hydroxypivalate ester compound is greater than 40% by weight, the plasticization efficiency and other properties of a cling film including the plasticizer composition may be degraded due to low tensile strength and high hardness.

In the compounds of formulae, $R_1$ and $R_2$ may be each independently a C6-C1 alkyl group, more preferably 1-ethylpentyl. $R_3$ and $R_4$ may be each independently a C6-C8 aryl group, and more preferably a phenyl group.

The hydroxypivalyl hydroxypivalate ester plasticizer composition according to an embodiment of the present invention may include 2-Ethyl-hexanoic acid 3-(2-ethyl-hexanolyoxy)-2,2-dimethyl-propyl ester (compound 1), Benzoic acid 3-(2-ethyl-hexanoyloxy)-2,2-dimethyl-propyl ester (compound 2), Benzoic acid 3-benzoyloxy-2,2-dimethyl-propyl ester (compound 3), 2-Ethyl-hexanoic acid 2-[3-(2-ethyl-hexanoyloxy)-2,2-dimethyl-propoxycarbonyl]-2-methyl-propyl ester (compound 4), Benzoic acid 2-[3-(2-ethyl-hexanoyloxy)-2,2-dimethyl-propoxycarbonyl]-2-methyl-propyl ester (compound 5), Benzoic acid 3-[3-(2-ethyl-hexanoyloxy)-2,2-dimethyl-propionyloxy]-2,2-dimethyl-propyl ester (compound 6), Benzoic acid 3-[3-(benzoyloxy)-2,2-dimethyl-propionyloxy]-2,2-dimethyl-propyl ester (compound 7), 2-Ethyl-hexanoic acid 2-{2-[3-(2-ethyl-hexanoyloxy)-2,2-dimethyl-propoxycarbonyl]-2-methyl-propoxycarbonyl}-2-methyl-propyl ester (compound 8), Benzoic acid 3-{3-[3-(2- ethyl-hexanoyloxy)-2,2-dimethyl-propionyloxy]-2,2-dimethyl-propionyloxy}-2,2dimethyl-propyl ester (compound 9), and Benzoic acid 3-{3-[3-(benzoyloxy)-2,2-dimethyl-propionyloxy]-2,2-dimethyl-propionyloxy}-2,2-dimethyl-propyl ester (compound 10).

The hydroxypivalyl hydroxypivalate ester plasticizer composition according to an embodiment of the present invention may be prepared by a method including reacting a hydroxypivalyl hydroxypivalate; or a mixture of a hydroxypivalyl hydroxypivalate and a neopentylglycol in an amount of 20 to

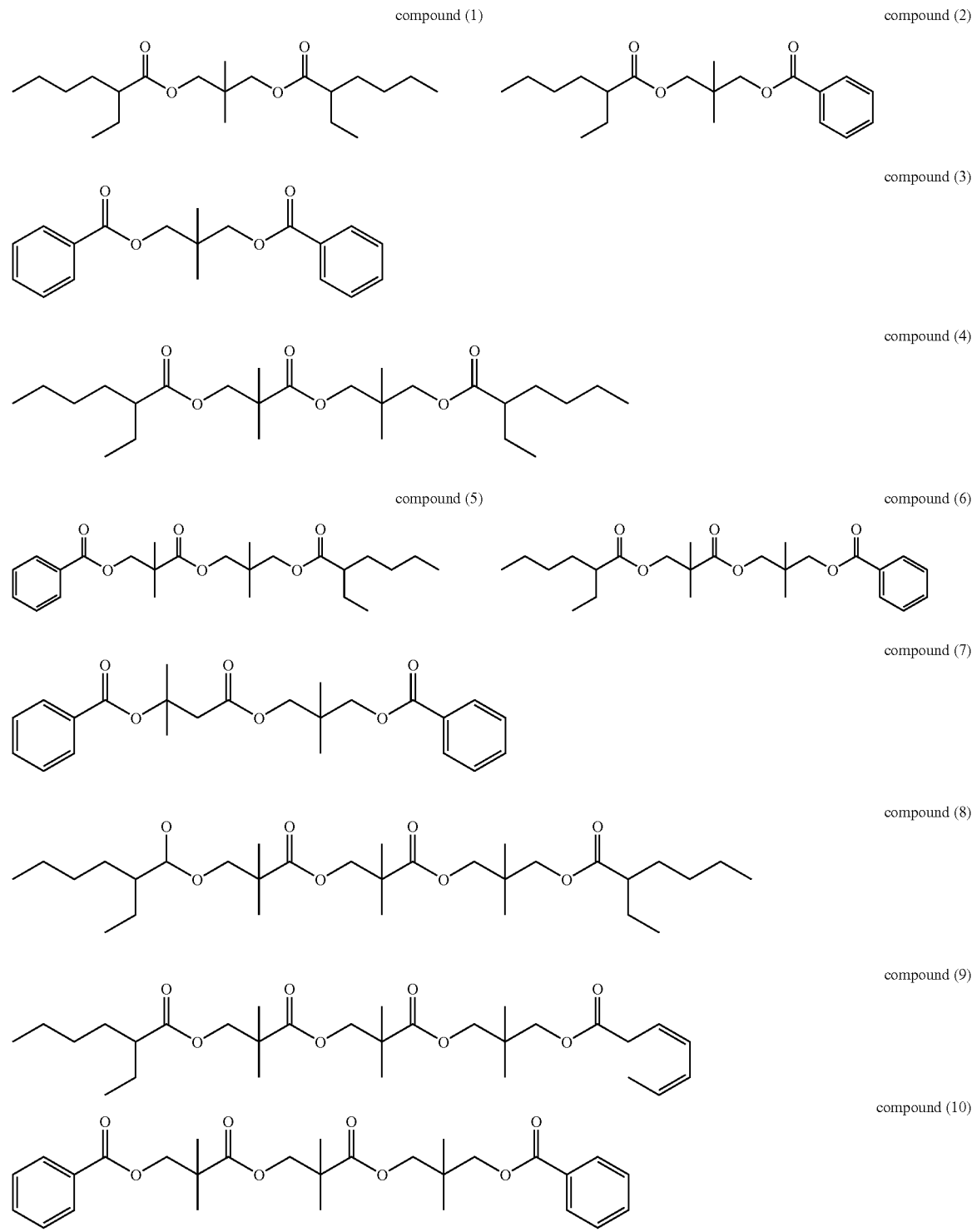

50% by weight with a C3-C12 aliphatic acid; a C6-C1 aromatic acid; or a C3-C12 aliphatic acid and a C6-C10 aromatic acid in an amount of 50 to 80% by weight.

The hydroxypivalyl hydroxypivalate and the neopentylglycol of the above mixture may be mixed in the weight ratio of 5:5 to 9.5:0.5. The aliphatic acid may have 6 to 10 carbon atoms and preferably be 2-ethylhexanoic acid, and the aromatic acid may have 6 to 8 carbon atoms and preferably be a benzoic acid.

A hydroxypivalyl hydroxypivalate ester plasticizer composition of an embodiment of the present invention can be obtained by reacting the reactants in the weight ratio described above.

That is, when a hydroxypivalyl hydroxypivalate is reacted with an aliphatic acid, a hydroxypivalyl hydroxypivalate ester composition containing compounds represented by formulae 1, 4 and 8 is obtained. When a hydroxypivalyl hydroxypivalate is reacted with an aromatic acid, a hydroxypivalyl hydroxypivalate ester containing compounds represented by 3, 7 and 10 is obtained. When a hydroxypivalyl hydroxypivalate is reacted with an aliphatic acid and an aromatic acid, a hydroxypivalyl hydroxypivalate ester containing compounds represented by formulae 1 through 10 is obtained. In order to obtain another composition, a desired compound can be separated from the composition containing the compounds of formulae 1 through 10 using a separation method that is well known in the art, wherein the separation method is not limited.

For example, a compound can be separated using a column chromatography. An adsorbent used as a stationary phase can be $Al_2O_3$, $SiO_2$, charcoal, $MgSiO_2$, or the like, all of which are well known in the art. In particular, the adsorbent can be a silica gel. However, the adsorbent is not limited to these materials. A mobile phase can be an organic solvent, such as n-hexane, ethylacetate, chloroform, or toluene, which is well known in the art. For example, the mobile phase can be n-hexane or ethylacetate. However, the mobile phase is not limited to these materials described above. Although the kind of solvent needed varies according to the polarity of a mixture to be separated and the polarity of a stationary phase required, in general, a solvent having a proper polarity obtained by mixing a solvent having high polarity and a solvent having low polarity in a proper ratio is used.

In the compounds of formulae, $R_1$ and $R_2$ may be a 1-ethyl pentyl group, and $R_3$ and $R_4$ may be a phenyl group, but are not limited thereto.

During the esterification reaction, various types of ester compounds are obtained since a transesterification occurs and produces by-products that are compounds of formulae 1 to 3 and 8 to 10. Transesterification occurs in a process of restructuring ester bonds contained in the hydroxypivalyl hydroxypivalate by an aliphatic acid and an aromatic acid.

The weight ratio of the aliphatic acid and the aromatic acid may be 1:99 to 99:1 when the hydroxypivalyl hydroxypivalate is reacted with the aliphatic acid and the aromatic acid.

The reactor may be a batch reactor, a mixed flow reactor, or a tubular reactor. However, the reactor is not limited thereto.

The esterification reaction may be performed at 100-300° C. for 4 to 14 hours. When the reaction temperature is less than 100° C., the reaction occurs very slowly so that a reaction product is inefficiently produced. On the other hand, when the reaction temperature is higher than 300° C., the reaction product decomposes and becomes discolored. When the reaction time is less than 4 hours, an insufficient amount of reaction occurs, and thus, the conversion and the product yield are low. On the other hand, when the reaction time is greater than 10 hours, the reaction almost reaches an equilibrium conversion rate and thus further reaction essentially stops.

The method may further include an entrainer. 1 to 20 parts by weight of a liquid entrainer based on 100 parts by weight of the reactant may be included in the reaction, or a gaseous entrainer may be added to the reactants at a flow rate of 0.1 to 10 times the volume of the reactor per hour. The entrainer is a substance that assists discharge of $H_2O$ generated as a by-product of the esterification out of the reaction. The removal of the generated $H_2O$ contributes to a shift of the reaction equilibrium aiding production of desired products because a reverse reaction of the esterification occurs less according to the Le Chatelier principle. Accordingly, the use of the entrainer results in an increase of the yield of the desired product. The entrainer can be an organic solvent, such as n-hexane, toluene, xylene; or an inert gas such as nitrogen gas. Preferably, the entrainer can be n-hexane, toluene, xylene, nitrogen gas, or the like. However the entrainer is not limited to these materials described above.

The method may further include a catalyst. The catalyst may be in an amount of 0.0001 to 1 parts by weight based on 100 parts by weight of the reactant. The catalyst promotes the esterification reaction. Examples of the catalyst include an acidic catalyst, such as sulfuric acid, hydrochloric acid, phosphoric acid, nitric acid, paratoluenesulfonic acid, methanesulfonic acid, alkyl sulfuric acid, or the like; a metal salt, such as aluminum sulfate, lithium fluoride, potassium chloride, cesium chloride, calcium chloride, ferric chloride, aluminum phosphorate, or the like; a metal oxide, such as heteropoly acid, or the like; natural/synthetic zeolite; cationic and anionic exchange resin; and an organic metal, such as tetra alkyl titanate, a polymer thereof, or the like. For example, the catalyst can be a paratoluenesulfonic acid or a tetraisopropyltitanate. However, the catalyst is not limited thereto.

The post treatment required after the completion of the esterification reaction is not limited. For example, an unreacted reactant material is removed through vacuum distillation, and then a neutralizing reaction is performed using a base solution, such as a NaOH, KOH, and $Na_2CO_3$ aqueous solution. Then the neutralization product is washed using water and selectively dehydrated under reduced pressure, and then an adsorbent is added thereto and then filtered.

A method of preparing a hydroxypivalyl hydroxypivalate ester plasticizer composition of an embodiment of the present invention will now be described in more detail.

A hydroxypivalyl hydroxypivalate; or a mixture of a hydroxypivalyl hydroxypivalate and a neopentylglycol in an amount of 20 to 50% by weight, a mixture of 2-ethylhexanoic acid and benzoic acid in an amount of 1 to 80% by weight, 1 to 20 parts by weight of xylene based on 100 parts by weight of the reactant as an entrainer, 0.0001 to 1 parts by weight of tetraisopropyltitanate based on 100 parts by weight of the reactant as a catalyst were added to a flask having a stirrer and a condenser, the temperature was increased to 220° C., and then the mixture was reacted for 4 to 14 hours. After the esterification, the flask was depressurized using a vacuum pump to remove un-reacted acid, and then a neutralizing reaction was performed using 5 to 50 parts by weight of NaOH aqueous solution based on 100 parts by weight of the reactant. The neutralization product was washed, dehydrated, and filtered. As a result, a hydroxypivalyl hydroxypivalate ester plasticizer composition was obtained.

A polyvinyl chloride resin having excellent properties of tensile strength, elongation, hardness, and migration resistance can be prepared using a hydroxypivalyl hydroxypivalate ester plasticizer composition according to an embodiment of the present invention. The polyvinyl chloride resin may be prepared using materials that are commonly used in a resin preparation in addition to the hydroxypivalyl hydroxypivalate ester plasticizer composition by a method that is commonly used for a resin preparation.

In addition, the hydroxypivalyl hydroxypivalate ester plasticizer composition according to an embodiment of the present invention may be applied to any resin besides the polyvinyl chloride resin to improve tensile strength, elongation, migration resistance, and hardness. Particularly, the hydroxypivalyl hydroxypivalate ester plasticizer composition is suitable for a polyvinyl chloride resin for a cling film used in food packing and can also be applied to a polyethylene foam sheet.

The present invention will be described in further detail with reference to the following examples. These examples are for illustrative purposes only and are not intended to limit the scope of the present invention.

EXAMPLES

The tensile strength, elongation, hardness, migration resistance and heating loss of polyvinyl chloride resin samples obtained in Examples and Comparative Examples were measured in the following manner. The results are shown in Table 2.

Tensile Strength

Based on ASTM D638, U.T.M was used to measure a tensile strength. Setting a cross head speed at 200 mm/min, a breaking point was measured. Tensile strength was calculated using an equation: Tensile Strength $(kgf/mm^2)$=Load (kgf)/{Thickness (mm)×Width (mm)}.

Elongation

Based on ASTM D638, U.T.M was used to measure an elongation. Setting a cross head speed at 200 mm/min, a breaking point of the sample was measured. Elongation was calculated using an equation: Elongation (%)={Extension/Initial length}×100.

Hardness

Hardness was measured to qualify plasticization efficiency. Based on ASTM D2240, a needle of a hardness tester (A type) was completely contacted to one site of a sample and after 5 minutes a hardness value was read. Five sites of respective samples were measured and their respective average values were obtained. The hardness was measured directly after the sample was prepared and one day after the sample was prepared.

Results of the tests described above are shown in Table 2.

Heat loss and migration resistance were measured in the following manner.

Heat loss

The composition was processed to prepare a 0.8 mm-thick sheet using a roll mill at 165° C. for 3 minutes. Then, 60 g of the 0.8 mm-thick sheet was processed to prepare a 0.4 mm-thick sample using a roll mill at 185° C. for 10 minutes. After 24 hours, the weight of the sample was measured and the heat loss was measured using an equation: Heat loss (wt %)={1−(weight of sample after being processed at 185° C. for 10 minutes)/60 g}×100.

Migration Resistance

An initial weight (Wi) of each sample was measured down to four decimal places and a 3 cm×3 cm sample sheet was placed between ABS resin plates in an oven at a temperature of 70° C. The result was placed under a 1 kg load for 72 hours, stored in a water bath over 4 hours, and then the weight (Wo) of the sample was measured to calculate the migration resistance using an equation: Migrated amount (wt %)={(Wi−Wo)/Wi}×100.

Example 1

(1) Preparation of Hydroxypivalyl Hydroxypivalate Ester Plasticizer Composition.

2 mol of hydroxypivalyl hydroxypivalate, 1.6 mol of 2-ethylhexanoic acid, 3.6 mol of benzoic acid, 60 g of xylene as an entrainer, 1.5 g of tetraisopropyltitanate as a catalyst were added to a 2L 4-neck round flask having a stirrer and a condenser, the temperature was increased to 220° C., and then the mixture was reacted for 8 hours.

After the esterification, the flask was depressurized to a pressure of 5 mmHg at 220° C. using a vacuum pump to remove un-reacted acid, and then a neutralizing reaction was performed using a 10 wt % NaOH aqueous solution. The neutralization product was washed using water and dehydrated, and an adsorbent was added thereto and filtered. As a result, a hydroxypivalyl hydroxypivalate ester plasticizer composition was obtained. The obtained hydroxypivalyl hydroxypivalate ester compound was analyzed, and the composition was found to be 0.4 wt % of 2-Etyl-hexanoic acid 3-(2-ethyl-hexanolyoxy)-2,2-dimethyl-propyl ester, 2.5 wt % of Benzoic acid 3-(2-ethyl-hexanoyloxy)-2,2-dimethyl-propyl ester, 4.3 wt % of Benzoic acid 3-benzoyloxy-2,2-dimethyl-propyl ester, 6.2 wt % of 2-Ethyl-hexanoic acid 2-[3-(2-ethyl-hexanoyloxy)-2,2-dimethyl-propoxycarbonyl]-2-methyl-propyl ester, 16.9 wt % of Benzoic acid 2-[3-(2-ethyl-hexanoyloxy)-2,2-dimethyl-propoxycarbonyl]-2-methyl-propyl ester, 14.6 wt % of Benzoic acid 3-[3-(2-ethyl-hexanoyloxy)-2,2-dimethyl-propionyloxy]-2,2-dimethyl-propyl ester, 44.9 wt % of Benzoic acid 3-[3-(benzoyloxy)-2,2-dimethyl-propionyloxy]-2,2-dimethyl-propyl ester, 0.6 wt % of 2-Ethyl-hexanoic acid 2-{2-[3-(2-ethyl-hexanoyloxy)-2,2-dimethyl-propoxycarbonyl]-2-methyl-propoxycarbonyl}-2-methyl-propyl ester, 2.7 wt % of Benzoic acid 3-{3-[3-(2-ethyl-hexanoyloxy)-2,2-dimethyl-propionyloxy]-2,2-dimethyl-propionyloxy}-2,2dimethyl-propyl ester, and 4.0 wt % of Benzoic acid 3-{3-[3-(benzoyloxy)-2,2-dimethyl-propionyloxy]-2,2-dimethyl-propionyloxy}-2,2-dimethyl-propyl ester.

The components and amount were identified using a gas chromatography mass spectrometer (GC-MS).

(2) Preparation of Polyvinyl Chloride Resin Using the Hydroxypivalyl Hydroxypivalate Ester Plasticizer Composition.

100 parts by weight of polyvinyl chloride (produced by LG Chemical Co., product name: LS100S) was blended with 60 parts by weight of the obtained hydroxypivalyl hydroxypivalate ester plasticizer composition as a plasticizer and 3 parts by weight of KP-630P produced by Korea Daehyup Co. Ltd. as a Ca—Zn stabilizer, and then the mixture was processed to form a 5 mm-thick sheet using a roll mill at 175° C. for 3 minutes. Then, the obtained sheet was preheated at 185° C. for 3 minutes, heated for 3 minutes, and then cooled for 3 minutes, using a pressing device, thereby forming a 1 mm-thick sheet. Subsequently, C type dumbbell-shaped samples were prepared from the 1 mm-thick sheet and tested.

Example 2

A hydroxypivalyl hydroxypivalate ester plasticizer composition was prepared in the same manner as in Example 1, except that the amount of the reactant materials used were changed as shown in Table 1. The obtained hydroxypivalyl hydroxypivalate ester composition was analyzed and the composition was found to be 1.4 wt %, 3.5 wt %, 2.2 wt %, 20.5 wt %, 19.8 wt %, 21.3 wt %, 20.0 wt %, 2.4 wt %, 5.1 wt %, and 2.5 wt % in the order of compounds 1 through 10, respectively.

Then, a sample of the hydroxypivalyl hydroxypivalate ester plasticizer composition obtained above was prepared in the same manner as in Example 1. The same tests as in Example 1 were performed on the prepared sample. The results are shown in Table 2.

Example 3

A hydroxypivalyl hydroxypivalate ester plasticizer composition was prepared in the same manner as in Example 1, except that the amount of the reactant materials used were changed as shown in Table 1. The obtained hydroxypivalyl hydroxypivalate ester composition was analyzed and the composition was found to be 2.2 wt %, 3.4 wt %, 1.4 wt %, 32.0 wt %, 19.5 wt %, 17.3 wt %, 10.6 wt %, 4.0 wt %, 5.1 wt %, and 1.6 wt % in the order of compounds 1 through 10, respectively.

Then, a sample of the hydroxypivalyl hydroxypivalate ester plasticizer composition obtained above was prepared in the same manner as in Example 1. The same tests as in Example 1 were performed on the prepared sample. The results are shown in Table 2.

Example 4

A hydroxypivalyl hydroxypivalate ester plasticizer composition was prepared in the same manner as in Example 1, except that the amount of the reactant materials used were changed as shown in Table 1. The obtained hydroxypivalyl hydroxypivalate ester composition was analyzed and the composition was found to be 4.2 wt %, 9.5 wt %, 5.1 wt %, 18.1 wt %, 20.9 wt %, 16.7 wt %, 18.8 wt %, 1.2 wt %, 2.7 wt %, 1.3 wt % in the order of compounds 1 through 10, respectively.

Then, a sample of the hydroxypivalyl hydroxypivalate ester plasticizer composition obtained above was prepared in the same manner as in Example 1. The same tests as in Example 1 were performed on the prepared sample. The results are shown in Table 2.

Example 5

A hydroxypivalyl hydroxypivalate ester plasticizer composition was prepared in the same manner as in Example 1, except that the amount of the reactant materials used were changed as shown in Table 1. The obtained hydroxypivalyl hydroxypivalate ester composition was analyzed and the composition was found to be 5.3 wt % of compound 1, 77.3 wt % of compound 4, 10.7 wt % of compound 8, and 6.7 wt % of other compounds. Here, the other compounds are not impurities but intermediates.

Then, a sample of the hydroxypivalyl hydroxypivalate ester plasticizer composition obtained above was prepared in the same manner as in Example 1. The same tests as in Example 1 were performed on the prepared sample. The results are shown in Table 2.

Example 6

A hydroxypivalyl hydroxypivalate ester plasticizer composition was prepared in the same manner as in Example 1, except that the amount of the reactant materials used were changed as shown in Table 1. The obtained hydroxypivalyl hydroxypivalate ester composition was analyzed and the composition was found to be 5.4 wt % of compound 3, 87.1 wt % of compound 7, 5.1 wt % of compound 10, and 2.4 wt % of other compounds. Here, the other compounds are not impurities but intermediates.

Then, a sample of the hydroxypivalyl hydroxypivalate ester plasticizer composition obtained above was prepared in the same manner as in Example 1. The same tests as in Example 1 were performed on the prepared sample. The results are shown in Table 2.

Comparative Example 1

A sample was prepared in the same manner as in Example 1, except that 60 parts by weight of di-2-ethylhexylphthalate (produced by LG Chemical Co., Ltd., product name: DOP), which is the most commonly used plasticizer, was used as a plasticizer, and 3 parts by weight of KP-630P produced by Korea Daehyup Co. Ltd. was used as a Ca—Zn stabilizer. The same tests as in Example 1 were performed on the prepared sample. The results are shown in Table 2.

Comparative Example 2

A sample was prepared in the same manner as in Example 1, except that di-2-ethylhexyladipate (produced by LG Chemical Co., Ltd., product name: DOA), which is a commonly used plasticizer, was used as a plasticizer. The same tests as in Example 1 were performed on the prepared sample. The results are shown in Table 2.

Comparative Example 3

A sample was prepared in the same manner as in Example 1, except that diisononylphthalate (produced by LG Chemical Co., Ltd., product name: DINP), which is a commonly used plasticizer, was used as a plasticizer. The same test as in Example 1 was performed on the prepared sample. The results are shown in Table 2.

Comparative Example 4

A sample was prepared in the same manner as in Example 1, except that diisononyladipate (produced by LG Chemical Co., Ltd., product name: DINA), which is a commonly used plasticizer, was used as a plasticizer. The same tests as in Example 1 were performed on the prepared sample. The results are shown in Table 2.

Comparative Example 5

A sample was prepared in the same manner as in Example 1, except that acetyl tri-butyric citrate (ATBC), which is commonly used in medical products as a non-phthalate-based plasticizer, was used as a plasticizer. The same tests as in Example 1 were performed on the prepared sample. The results are shown in Table 2.

TABLE 1

|  |  | Example 1 | Example 2 | Example 3 | Example 4 | Example 5 | Example 6 |
|---|---|---|---|---|---|---|---|
| Reactant materials | Hydroxypivalyl hydroxypivalate (mol) | 2 | 2 | 2 | 1.8 | 2 | 2 |
|  | Neopentylglycol (mol) | — | — | — | 0.39 | — | — |
|  | 2-ethylhexanoic acid (mol) | 1.6 | 3 | 3.6 | 3.29 | 5.2 | — |
|  | Benzoic acid (mol) | 3.6 | 2.2 | 1.6 | 2.41 | — | 5.2 |
|  | Xylene (g) | 60 | — | — | — | — | 60 |
| Tetraisopropyltitanate (g) |  | 1.5 | 1.5 | 1.5 | 1.5 | 1.5 | 1.5 |

TABLE 2

|  | Tensile strength (kg/cm$^2$) | Elongation (%) | Heat loss (wt %) | Migration resistance (wt %) | Hardness |
|---|---|---|---|---|---|
| Example 1 | 2.13 | 408 | 2.45 | 0.27 | 74.9 |
| Example 2 | 2.11 | 412 | 2.51 | 0.31 | 74.8 |
| Example 3 | 1.74 | 415 | 2.52 | 0.38 | 74.6 |
| Example 4 | 2.12 | 416 | 1.74 | 0.63 | 74.4 |
| Example 5 | 1.72 | 420 | 3.05 | 0.88 | 73.5 |
| Example 6 | 2.02 | 409 | 2.82 | 0.72 | 75.6 |
| Comparative Example 1 | 1.75 | 397 | 2.14 | 0.26 | 74.5 |
| Comparative Example 2 | 1.71 | 392 | 3.62 | 0.72 | 73.9 |
| Comparative Example 3 | 1.83 | 419 | 2.01 | 0.41 | 75.2 |
| Comparative Example 4 | 1.91 | 410 | 2.86 | 0.64 | 74.6 |
| Comparative Example 5 | 2.08 | 422 | 4.15 | 0.60 | 74.0 |

As shown in Table 2, plasticizer compositions of Examples 1 through 6 that were obtained according to an embodiment of the present invention have more excellent properties of tensile strength, elongation, heat loss, and migration resistance compared to those of Comparative Examples. Hardness of the Examples 1 through 6 are similar to the Comparative Examples.

The hydroxypivalyl hydroxypivalate ester plasticizer composition of the present invention can be used as a plasticizer during polyvinyl chloride manufacturing process to provide a polyvinyl chloride having excellent properties of heat loss, migration resistance, and plasticization efficiency. In addition, tensile strength, elongation, etc. are improved.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A hydroxypivalyl hydroxypivalate ester compound selected from the group represented by formulae 5 through 10:

$$R_3OCO—CH_2C(CH_3)_2—COO—CH_2C(CH_3)_2—CH_2—OCOR_2 \quad (5)$$

$$R_2OCO—CH_2C(CH_3)_2—COO—CH_2C(CH_3)_2—CH_2—OCOR_3 \quad (6)$$

$$R_4OCO—CH_2C(CH_3)_2—COO—CH_2C(CH_3)_2—CH_2—OCOR_4 \quad (7)$$

$$R_1OCO—CH_2C(CH_3)_2—COO—CH_2C(CH_3)_2—COO—CH_2C(CH_3)_2—CH_2—OCOR_1 \quad (8)$$

$$R_2OCO—CH_2C(CH_3)_2—COO—CH_2C(CH_3)_2—COO—CH_2C(CH_3)_2—CH_2—OCOR_3 \quad (9)$$

$$R_4OCO—CH_2C(CH_3)_2—COO—CH_2C(CH_3)_2—COO—CH_2C(CH_3)_2—CH_2—OCOR_4 \quad (10)$$

where, $R_1$ and $R_2$ are each independently a C3-C12 alkyl group and $R_3$ and $R_4$ are each independently a C6-C10 aryl group.

2. The hydroxypivalyl hydroxypivalate ester compound of claim 1, wherein $R_1$ and $R_2$ are a 1-ethylpentyl group, and $R_3$ and $R_4$ are a phenyl group.

3. A hydroxypivalyl hydroxypivalate ester plasticizer composition comprising:
   a neopentylglycol ester compound comprising at least one of the compounds represented by formulae 1 through 3;
   a hydroxypivalyl hydroxypivalate ester compound comprising at least one of the compounds represented by formulae 4 through 7; and
   a hydroxypivalyl hydroxypivalate ester compound comprising at least one of the compounds represented by formulae 8 through 10:

$$R_1OCO—CH_2C(CH_3)_2CH_2—OCOR_1 \quad (1)$$

$$R_2OCO—CH_2C(CH_3)_2CH_2—OCOR_3 \quad (2)$$

$$R_4OCO—CH_2C(CH_3)_2CH_2—OCOR_4 \quad (3)$$

$$R_1OCO—CH_2C(CH_3)_2COO—CH_2C(CH_3)_2CH_2—OCOR_1 \quad (4)$$

$$R_3OCO—CH_2C(CH_3)_2—COO—CH_2C(CH_3)_2CH_2—OCOR_2 \quad (5)$$

$$R_2OCO—CH_2C(CH_3)_2—COO—CH_2C(CH_3)_2CH_2—OCOR_3 \quad (6)$$

$$R_4OCO—CH_2C(CH_3)_2—COO—CH_2C(CH_3)_2CH_2—OCOR_4 \quad (7)$$

$$R_1OCO—CH_2C(CH_3)_2—COO—CH_2C(CH_3)_2—COO—CH_2C(CH_3)_2—CH_2—OCOR_1 \quad (8)$$

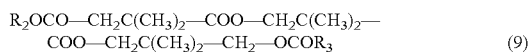

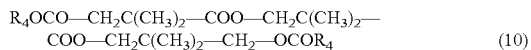

where, $R_1$ and $R_2$ are each independently a C3-C12 alkyl group, and $R_3$ and $R_4$ are each independently a C6-C10 aryl group.

4. The hydroxypivalyl hydroxypivalate ester plasticizer composition of claim 3 comprising 1 to 50% by weight of the neopentylglycol ester compound comprising at least one of the compounds represented by formulae 1 through 3; 40 to 90% by weight of the hydroxypivalyl hydroxypivalate ester compound comprising at least one of the compounds represented by formulae 4 through 7; and 1 to 40% by weight of the a hydroxypivalyl hydroxypivalate ester compound comprising at least one of the compounds represented by formulae 8 through 10.

5. The hydroxypivalyl hydroxypivalate ester plasticizer composition of claim 3 comprising 2-Ethyl-hexanoic acid 3-(2-ethyl-hexanolyoxy)-2,2-dimethyl-propyl ester, Benzoic acid 3-(2-ethyl-hexanoyloxy)-2,2-dimethyl-propyl ester, Benzoic acid 3-benzoyloxy-2,2-dimethyl-propyl ester, 2-Ethyl-hexanoic acid 2-[3-(2-ethyl-hexanoyloxy)-2,2-dimethyl-propoxycarbonyl]-2-methyl-propyl ester, Benzoic acid 2-[3-(2-ethyl-hexanoyloxy)-2,2-dimethyl-propoxycarbonyl]-2-methyl-propyl ester, Benzoic acid 3-[3-(2-ethyl-hexanoyloxy)-2,2-dimethyl-propionyloxy]-2,2-dimethyl-propyl ester, Benzoic acid 3-[3-(benzoyloxy)-2,2-dimethyl-propionyloxy]-2,2-dimethyl-propyl ester, 2-Ethyl-hexanoic acid 2-{2-[3-(2-ethyl-hexanoyloxy)-2,2-dimethyl-propoxycarbonyl]-2-methyl-propoxycarbonyl}-2-methyl-propyl ester, Benzoic acid 3-{3-[3-(2-ethyl-hexanoyloxy)-2,2-dimethyl-propionyloxy]-2,2-dimethyl-propionyloxy}-2,2dimethyl-propyl ester, Benzoic acid 3-{3-[3-(benzoyloxy)-2,2-dimethyl-propionyloxy]-2,2-dimethyl-propionyloxy}-2,2-dimethyl-propyl ester.

6. A method of preparing a hydroxypivalyl hydroxypivalate ester plasticizer composition of claim 3, comprising reacting a hydroxypivalyl hydroxypivalate; or a mixture of a hydroxypivalyl hydroxypivalate and a neopentylglycol in an amount of 20 to 50% by weight with a C3-C12 aliphatic acid; a C6-C10 aromatic acid; or a C3-C12 aliphatic acid and a C6-C10 aromatic acid in an amount of 50 to 80% by weight.

7. The method of claim 6, wherein the hydroxypivalyl hydroxypivalate and the neopentylglycol are mixed in the weight ratio of 5:5 to 9.5:0.5.

8. The method of claim 6, wherein the aliphatic acid is 2-ethylhexanoic acid, and the aromatic acid is a benzoic acid.

9. The method of claim 6, wherein the reaction is performed at 100 to 3000 C for 4 to 14 hours.

10. The method of claim 6, wherein 1 to 20 parts by weight of a liquid entrainer based on 100 parts by weight of the reactant is further comprised in the reaction, or a gaseous entrainer is added to the reactants at a flow rate of 0.1 to 10 times the volume of the reactor per hour.

11. The method of claim 10, wherein the entrainer is selected from the group consisting of n-hexane, toluene, xylene, nitrogen and helium.

12. The method of claim 6, wherein 0.0001 to 1 parts by weight of a catalyst based on 100 parts by weight of the reactant is further added to the reaction.

13. The method of claim 12, wherein the catalyst is para-toluene sulfonic acid or tetraisopropyltitanate.

14. A polyvinyl chloride resin comprising the hydroxypivalyl hydroxypivalate ester plasticizer composition of claim 3.

15. A polyvinyl chloride resin comprising the hydroxypivalyl hydroxypivalate ester plasticizer composition of claim 4.

16. A polyvinyl chloride resin comprising the hydroxypivalylhydroxypivalate ester plasticizer composition of claim 5.

* * * * *